United States Patent
Veith et al.

(10) Patent No.: US 6,633,375 B1
(45) Date of Patent: Oct. 14, 2003

(54) METHOD AND DEVICE FOR OPTICALLY EXAMINING STRUCTURED SURFACES OF OBJECTS

(75) Inventors: Michael Veith, Wetzlar (DE); Volker Knorz, Huettenberg (DE); Edgar Maehringer-Kunz, Muenster-Sarmsheim (DE)

(73) Assignee: Leica Microsystems Semiconductor GmbH, Wetzlar (DE)

( * ) Notice: Subject to any disclaimer, the term of this patent is extended or adjusted under 35 U.S.C. 154(b) by 0 days.

(21) Appl. No.: 09/647,497

(22) PCT Filed: Jan. 27, 2000

(86) PCT No.: PCT/DE00/00256

§ 371 (c)(1),
(2), (4) Date: Sep. 29, 2000

(87) PCT Pub. No.: WO00/45196

PCT Pub. Date: Aug. 3, 2000

(30) Foreign Application Priority Data

Jan. 29, 1999 (DE) .......................... 199 03 486

(51) Int. Cl.⁷ .................. G01N 21/00; G01N 21/86; H04N 9/47; G06K 9/00
(52) U.S. Cl. ............... 356/237.4; 250/559.41; 348/128; 382/144; 382/145
(58) Field of Search ............ 556/237.4, 237.5, 556/237.1, 237.3; 348/125, 128, 126; 382/141, 144, 145, 149, 147; 250/559.43, 559.41, 559.45

(56) References Cited

U.S. PATENT DOCUMENTS

| | | | |
|---|---|---|---|
| 4,585,315 A | 4/1986 | Sincerbox et al. | 350/525 |
| 4,595,289 A | 6/1986 | Feldman et al. | 356/237 |
| 4,644,172 A * | 2/1987 | Sandland et al. | 250/458.1 |
| 4,681,442 A | 7/1987 | Wagner | 356/237 |
| 4,720,191 A | 1/1988 | Siegel et al. | 356/237 |
| 4,881,802 A * | 11/1989 | Stankewitz | 359/387 |
| 5,134,278 A | 7/1992 | Nelen | 250/223 B |
| 5,278,012 A * | 1/1994 | Yamanaka et al. | 430/30 |
| 5,293,538 A * | 3/1994 | Iwata et al. | 356/239.1 |
| 5,343,290 A * | 8/1994 | Batchelder et al. | 356/237.3 |
| 5,455,870 A * | 10/1995 | Sepai et al. | 348/126 |

(List continued on next page.)

FOREIGN PATENT DOCUMENTS

| | | | | |
|---|---|---|---|---|
| DE | 2 021 784 | | 11/1970 | |
| DE | 23 31 750 | | 1/1975 | |
| DE | 37 14 830 | | 11/1988 | |
| DE | 689 23 353 | | 4/1996 | |
| EP | 0 387 930 | | 9/1990 | |
| JP | 54103362 A | * | 8/1979 | G02B/21/36 |
| WO | WO 98/20327 | | 5/1998 | |

Primary Examiner—Zandra V. Smith
Assistant Examiner—Gordon J Stock
(74) Attorney, Agent, or Firm—Crowell & Moring LLP

(57) ABSTRACT

A method and an apparatus are described for the optical examination of structured surfaces of objects, especially of wafers and/or masks. The optical apparatus has an observation beam path (6) whose central axis (42) is directed vertically against the surface of the object (16), an illumination beam (2) whose central ray (40) falls vertically on the surface of the object, and an illumination beam (3) whose central ray (41) falls obliquely onto the surface of the object (16). In the observation beam path (6) the image of the surface of the object (6) is observed and/or detected. In the observation beam path (6) a filter device (38) and/or detector device (18) is disposed. The optical system has an illumination device (39) for the simultaneous production of a dark field illumination, a device for the coding (11) of the illumination beams (2, 3) being associated with the bright field (2) and/or the dark field illumination beam (3).

3 Claims, 3 Drawing Sheets

U.S. PATENT DOCUMENTS

| | | | | |
|---|---|---|---|---|
| 5,515,163 A | * | 5/1996 | Kupershmidt et al. | 356/338 |
| 5,515,452 A | * | 5/1996 | Penkethman et al. | 382/141 |
| 5,719,704 A | * | 2/1998 | Shiraishi et al. | 359/558 |
| 5,805,278 A | | 9/1998 | Danko | 356/237 |
| 5,822,055 A | * | 10/1998 | Tsai et al. | 250/559.39 |
| 5,883,714 A | * | 3/1999 | Jann et al. | 356/237.2 |
| 5,917,588 A | * | 6/1999 | Addiego | 356/237.2 |
| 5,982,493 A | * | 11/1999 | Lehnen et al. | 250/559.23 |
| 5,997,164 A | * | 12/1999 | Betts et al. | 362/554 |
| 6,122,047 A | * | 9/2000 | Stover et al. | 356/237.3 |
| 6,201,601 B1 | * | 3/2001 | Vaez-Iravani et al. | 356/237.4 |

* cited by examiner

METHOD AND DEVICE FOR OPTICALLY EXAMINING STRUCTURED SURFACES OF OBJECTS

BACKGROUND OF THE INVENTION

The invention relates to a method for the optical study of structured surfaces of objects, especially of wafers and/or masks, with an observation beam path whose central axis is directed perpendicularly against the surface of the object, with an illuminating beam whose central ray falls perpendicularly on the surface of the object, and with an illuminating beam whose central ray falls obliquely on the surface of the object, while in the observation light path the image of the surface of the object is observed and/or detected, and to an apparatus for the practice of this method.

In optical inspection technology, complex structures on flat substrates are inspected in an image field. This is the case especially in the semiconductor industry for the optical inspection of the structured surfaces of wafers and masks. Any defects present, for example, are to be detected and classified and/or extremely small textural widths ("critical dimensions") are to be examined and measured. Defects on the structured surfaces may be, for example, grains of dust, small air inclusions in the resist, resist residues on the wafers, broken edges, etc.

The study is performed, for example, with an optical apparatus and with illumination in which the central ray of the illuminating beam falls perpendicularly onto the surface of the object. Such an inspection device is, for example, embodied in a microscope with a Kohler bright field illuminating system.

It has been found, however, that the detection of defective edges, point defects, defects at corners and boundaries of raised and recessed structures with a bright-field illumination often is insufficient. For this reason recourse has been taken to an additional inspection with an illuminating beam whose central ray strikes obliquely onto the surface of the object. Such illumination is achieved, for example, in a microscope with a dark field illuminating system. This illumination is especially suited for the detection of the defective structures described. In the case of this dark field illumination, however, no surfaces are visible. The edges and structures appear in rich contrast as bright lines on a dark background. Irregularities in these lines indicate a defective edge or structure.

Illumination apparatus for a microscope are disclosed in DE-OS 20 21 784 and DE 23 31 750 C3, in which it is possible to shift as desired from bright field to dark field illumination. In both illumination apparatus, in the illuminating beam there are provided, among other things, a light source, adjustable diaphragms, an annular diaphragm with a center stop that can be turned in and out, and an objective with an annular mirror around the objective. The annular diaphragm is transparent and the center stop is opaque. By turning in the center stop the change is made from a bright field to a dark field illumination. The light is no longer thrown on the object through the objective, but only through the annular mirror. The central rays of the illuminating beam no longer strike perpendicularly onto the surface of the object but strike it obliquely. Both microscopes are equipped each with a common observation light path for the bright field and the dark field illumination.

In neither of the disclosures is any simultaneous bright field and dark field illumination provided.

EP 0 183 946 B1 discloses a combined bright field/dark field illumination device with two light sources, in which the change from bright field to dark field illumination is performed through mechanical locks. One lock is associated with each light source. In this device it is also provided such that both kinds of illumination are applied simultaneously. For this purpose both locks are opened. But it not stated in this disclosure what special advantages result from this mixed lighting. No coding and later decoding of the bright field and/or the dark field illumination beam takes place.

DE 37 14 830 A1 discloses a combined bright field/dark field reflected light illumination for a microscope in which the change from bright field to dark field illumination is performed by an insertable center stop. Furthermore, in the dark field beam path an optical element of annular construction is provided with individual lens crown surfaces arranged side by side. These lens crown surfaces can have different spectral transmittance. In this illuminating device, however, no simultaneous bright field and dark field illumination is provided. Here, again, it is not stated what special advantages result from such colored illumination.

An optimized inspection method for the optical testing of structured surfaces of objects with a microscope having a combination of bright field and dark field illumination uses the two illumination methods one after the other. This resulting manual changing of the lighting conditions not only causes a doubling of the time is required for image capture and inspection, but also an additional manual manipulation of the center stop on the microscope.

SUMMARY OF THE INVENTION

It is therefore the object of the present invention to provide a method and an apparatus for the optical inspection of structured surfaces of objects, in which the measuring and inspection time with a bright field illumination beam and a dark field illumination beam is minimized.

This object is achieved in the method of the invention in that at least one of the two illuminating beams is provided with coding and the surface of the object is lighted simultaneously by both illumination beams, and in the observation light path the images produced by the different illumination beams are separated from one another and presented for observation and/or evaluation.

This object is achieved in the apparatus of the invention in that an optical system with a filter device and/or detector device and an illumination device arranged in the observation light path is provided for the simultaneous generation of a bright field and a dark field illumination, a system being associated with the bright field and/or the dark field illumination beam for the purpose of coding to distinguish the illumination beams.

Additional advantageous embodiments of the invention are described hereinafter.

With the invention it is accomplished that the object is illuminated simultaneously with a bright field beam and a dark field light beam. At least one of the two beams is coded by color, polarization or modulation. The separation of the illumination beams reflected from the object takes place in the common observation beam path through a corresponding filter device and/or a corresponding detector device.

For example, the prepared object can be illuminated in the dark field at a low angle of incidence, with red light for example, and simultaneously with green/blue within the aperture cone of the objective, with the remaining visible color spectrum. Since the light in the common observation beam path is again mixed in the colors, a separation by color takes place in the observation light path, e.g., by a dichroic splitter followed by imaging to separate black-and-white CCD cameras.

An RGB-CCD camera can also be provided directly in the observation light path. The two light paths are then separated by a computer-based processing of the RGB channels.

In another embodiment of the invention, the illuminating apparatus has a common light source or at least two separate light sources for the simultaneous production of the bright field and dark field illumination.

In a simple embodiment of the invention, the surface of the object is illuminated in the bright field with normal white light and the oblique illumination beams of the dark field are created by a single light source which emits red light and is positioned laterally on the object. The separation of the two images that follows is performed in the observation beam path with a filtering and/or detecting apparatus.

The apparatus for coding the illumination beam can have, for example, a color filter, a polarizing filter, a modulation filter or a dichroic splitter. However, provision is also made for the use of colored light sources or light sources with a one-color or monochromic emission characteristic. The associated filter set-up can be equipped, for example, with a color filter, a polarizing filter, a demodulation filter or a dichroic splitter.

The detector device can also be configured such that at least one CCD element is present, which is configured as a black-and-white or color camera. In the case of an RBG camera and a color identification of the illuminating beams there is no necessity of an additional filter device for the separation into a bright-field or dark-field image, since the RGB channels can be read separately.

The detector device in an additional embodiment of the invention is connected electrically or electronically to a computer system. The computer system then has a plurality of computers operating in parallel for the simultaneous detection and/or evaluation of the images. With the computers working in parallel, different processing steps of image detection, image analysis or inspection, error analysis, error classification and metrology (measurement of structure widths) can be performed simultaneously. Parallel processing accordingly reduces the inspection time for a single object.

In another embodiment of the invention the optical system can be in the form of a microscope. A Kohler illumination system is advantageously provided in the microscope. This illumination system can be configured as a top lighting or substage lighting system.

In another embodiment of the invention, several differently coded dark field beam paths can be provided. The differently coded dark field beam paths can also illuminate the object from different angles.

BRIEF DESCRIPTION OF THE DRAWINGS

The invention is further explained with reference to working embodiments in conjunction with the schematic drawing.

DETAILED DESCRIPTION OF PREFERRED EMBODIMENTS

Figure 1:
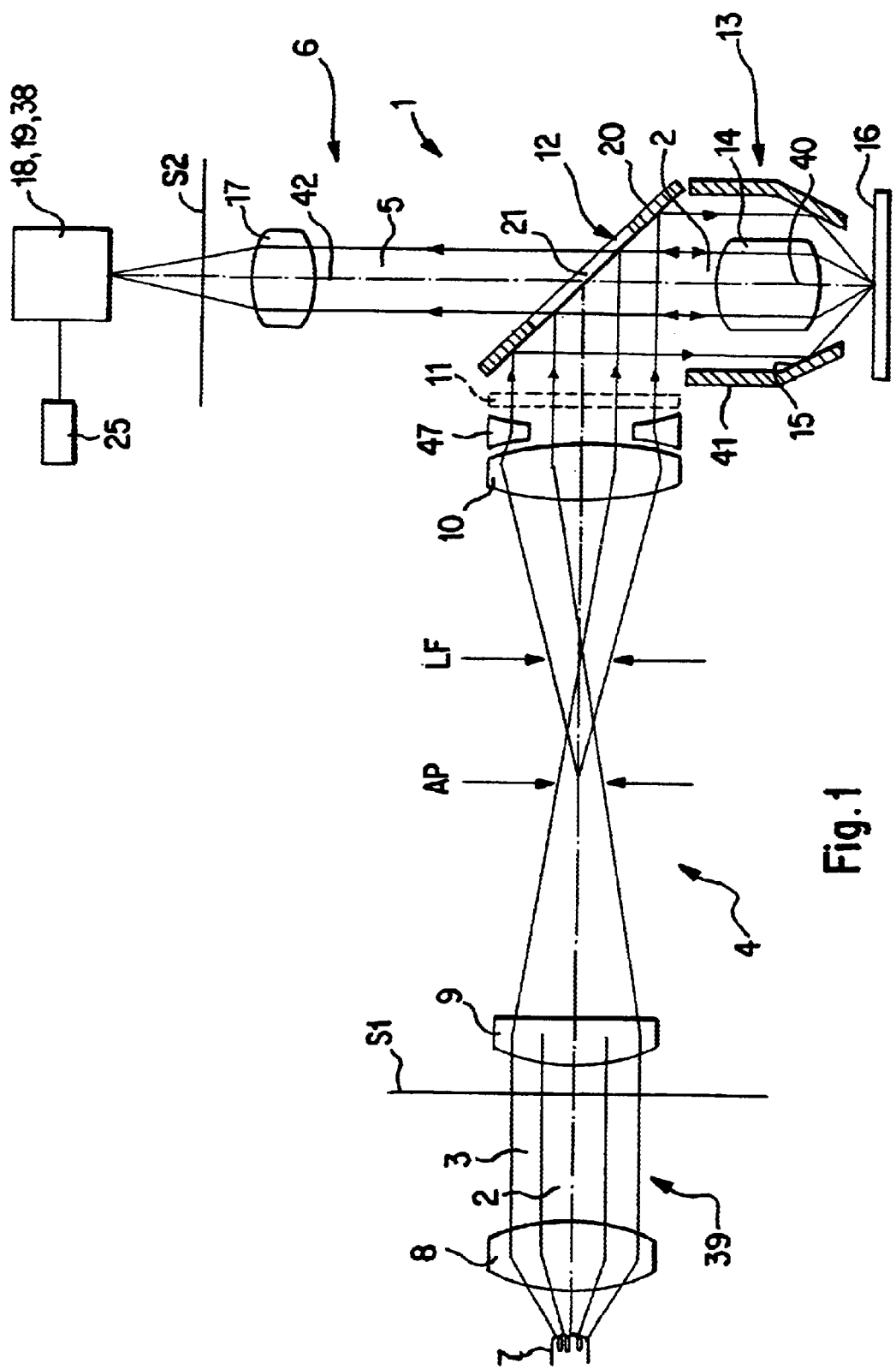
FIG. 1: is a simultaneous bright field and dark field illuminating system of a reflected-light microscope with its observation light path

FIG. 1 shows an illuminator of a microscope 1 in reflected light operation, with an illuminating beam path 4 and an observation light path 6. In the illuminating beam path, starting from a light source 7 followed by a condenser 8, a bright field illumination beam 2 and a dark field illumination beam 3 are represented. The two beams 2 and 3 pass through an illumination lens 9, and aperture diaphragm plane AP with controllable aperture, and a condenser lens 10. Before the two beams strike a coding system 11, the dark field illumination beam 3 passes through a dark field ring lens 47.

The coding device 11 is configured such that the two beams 2 and 3 are given a different identification characteristic. For this purpose, the coding device 11 is equipped with a color filter or a polarizing filter or a modulation filter or a dichroic splitter.

As an alternative to the coding system 11, the identification of the dark field and/or bright field light beams can be established at the plane AP of the aperture diaphragm if the latter is made of colored glass and/or a thin-layer color filter.

Further on in the illuminating beam path 4, there is a splitter mirror 12. The splitter mirror 12 has an outer, fully silvered ring 20 to reflect the dark field beam 3 and an inner partially silvered circle 21 to reflect the bright field beam 2 and to transmit the observation beam 5.

The reflected bright field illumination beam 2 is passed through an objective lens system 14 of a dark field objective 13 and illuminates the surface of an object 16. The central ray of the bright field beam 2 strikes perpendicularly the surface of the object 16. The axis of the central ray 40 of the bright field beam 2 and the axis of the central ray 42 of the observation beam path 5 have the same alignment.

The dark field beam 3 reflected from the splitter mirror 12 passes around the objective lens system 14 of dark field objective 13 and strikes the ring mirror 15. From there the dark field beam 3 is turned against the object 16. At the same time the central ray of the dark field beam strikes the surface of the object 16 obliquely. Since the cross section of the dark field beam 3 is ring-shaped, here all of the central rays 41 from the ring strike the surface of the object 16, obliquely.

The observation beam 5 issuing from the object 16 is carried in the observation beam path 6 through the objective lens system 14, the splitter mirror 12 and the tube lens 17 and strikes a filter 38 and/or detector device 18. In the present embodiment, this detector device 18 is constructed in the form of a CCD color camera 19. The detector device 18 is connected electrically to a computer system 25.

The two illuminating beams 2 and 3 pass in the illuminating beam path 4 through the coding system 11. This can consist, for example, of a combination color filter with a blue inner circle for the bright field beam 2 and a red ring surrounding the blue circle for the dark field illumination beam 3 (cf. FIG. 4). The two beams are there provided with different coding characteristics and being thus coded impinge simultaneously against the object 16. In the common observation beam 5 the two colored beams are mixed. By means of the detector device 18 with the color camera 19 and the computer system 25 the two images are electronically separated. In this embodiment the filter device 38 can be omitted.

By reading the blue color portion, the bright field image of the object 16 is produced and by reading the red color portion the dark field image of the object 16 is produced. With the computer system 25 these two images are then processed in parallel for defect analysis, defect classification and structure measurement.

It is evident that the identification device is not limited to a combination red and blue filter. Any kind of identification can be used in the illumination beams if a corresponding decoding system is available in the form of a filter and/or detector device.

The coding means 11 represented in FIG. 1 is not bound to a specific location within the illumination beam path 4. The coding device 11 can also be provided in the vicinity of the aperture diaphragm AP, near the interface S1 or it can be a dichroic coating on the partially light permeable mirror 12 or the ring mirror 15 of the dark field objective 13.

Neither is the invention limited to a single light source 7. At the interface S1 an illumination system of two or more light sources, for example, can be arranged.

Figure 2:
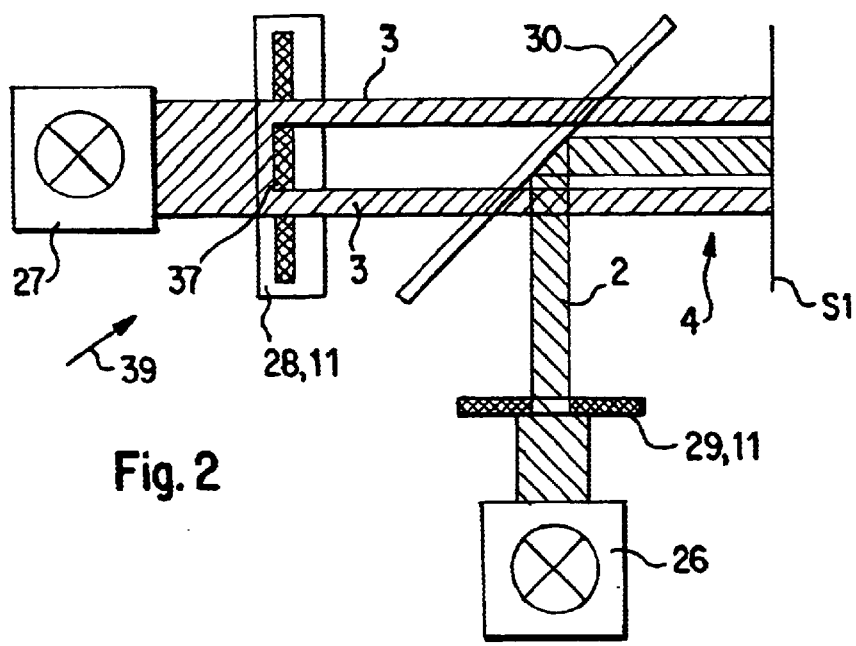
FIG. 2: an illuminator with two light sources and system for coding the illuminating beams

FIG. 2 shows such an illumination system with two light sources 26 and 27. Light source 26 is associated with a diaphragm 29 to produce the dark field beam 3, the illumination light being reflected through an additional partially silvered mirror 30 into the illumination beam path 4. A diaphragm 28 with an opaque center stop 37 is associated with the light source 27 to produce the bright field beam 2, the light being passed through the central part of the additional partly silvered mirror 30 into the illumination beam path 4.

The coding device 11 can here be also a component of the two diaphragms 28 and 29, and also replace one or both diaphragms. Furthermore, the additional splitter mirror 30 can be configured as a coding device and use, for example, a dichroic coating on the splitter mirror.

Figure 3:
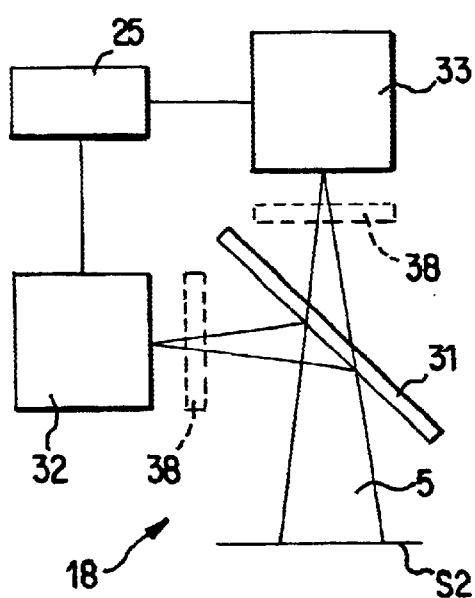
FIG. 3: a detector device with two CCD elements preceded by a filtering system

FIG. 3 shows an embodiment of a filter device 38 followed by a detector 18 with two black-and-white cameras 32 and 33, with an additional splitter mirror 31 which here again can be a dichroic mirror. Through the common interface S2 the detector device can be integrated with the filter device into the observation beam path of FIG. 1. The two black-and-white cameras 32 and 33 are each connected to the computer system 25. The filter device 38 is equipped corresponding to the coding device 11 with a color filter, a polarizing filter, a demodulating filter and a dichroic splitter.

In the present invention it is not necessary, either, that the two illumination beams be coded by a coding device with red and blue light, for example. In many applications it is sufficient if, for example, only the dark field beam is coded and the bright field beam continues to contain white light.

Applications are also possible, however, in which a single code for the dark field beam or the bright field beam is not sufficient. In these cases the single dark field beam and/or the bright field beam are provided, for example, both with a color code and with polarization code. It is also conceivable, however, for the dark field and/or the bright field beam to be provided with frequency modulation by means of a chopper or the like.

Figure 4:
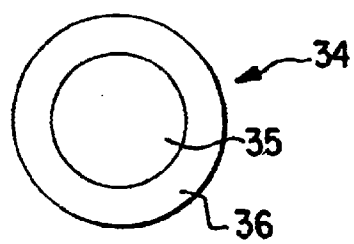
FIG. 4: a color filter of the filtering system

FIG. 4 shows an embodiment of the coding device with a combination color filter 34 which is provided with a blue inner circle 35 for the bright field beam and with an outer red ring 36 for the dark field beam. The filter 34, however, can have other combinations of modulator and/or color filter and/or polarization filter.

Figure 5:
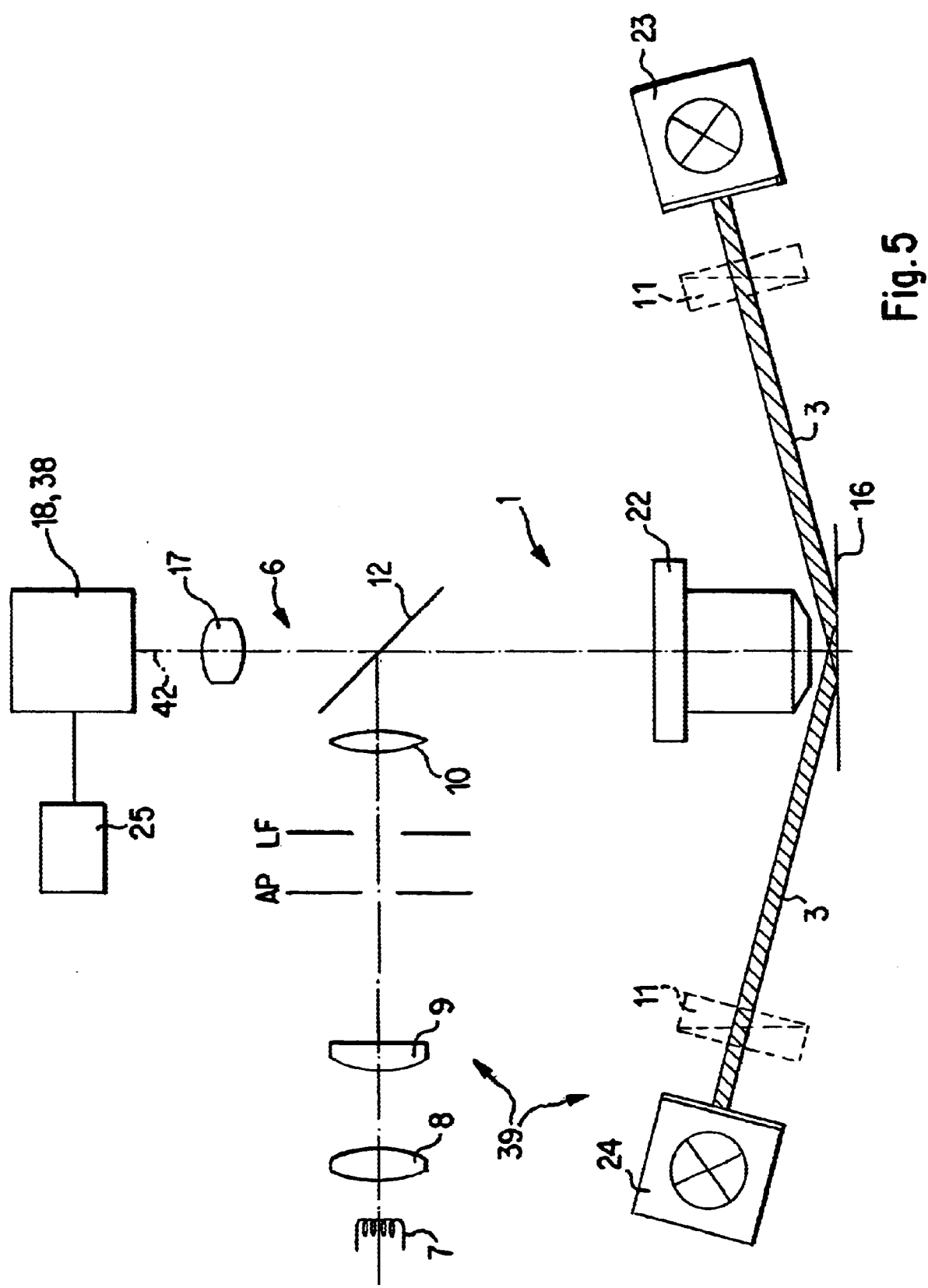
FIG. 5: a simultaneous bright field and dark field illumination apparatus of a reflected light microscope and with externally arranged light sources for dark field lighting

FIG. 5 shows an illumination apparatus of the microscope according to FIG. 1. The illumination apparatus integrated in microscope 1 with light source 7 is configured as a normal bright field illuminator. In contrast to the embodiment in FIG. 1, a bright field objective 22 is also used here. The bright field beam in this embodiment is similar to the described bright field beam of FIG. 1. The dark field beam 3 is here produced by two light sources 23 and 24 arranged externally on the microscope stand, not shown. A coding device 11 is associated with both light sources 23 and 24.

The observation beam 6 is configured like the beam already described with the filter 38 and/or detector device 18 to which the computer system 25 is connected. The light source for the dark field beam, therefore, does not need to be integrated into the optical system. For the practice of the method of the invention it also suffices if only a single externally disposed light source 23 or 24 is provided for the dark field beam 3.

Figure 6:
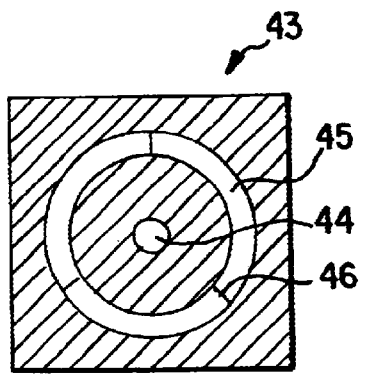
FIG. 6: a combination aperture diaphragm

FIG. 6 shows a combination aperture diaphragm 43 with a circular opening 44 for the bright field illumination and with an annular opening 45 for the dark field illumination. Bridges 46 are provided for holding the opaque part between the two openings 44 and 45. Both openings 44 and 45 can have a glass or plastic color filter. This combination aperture diaphragm can be arranged in plane AP (FIGS. 1 and 5).

List of Reference Characters

AP—Aperture diaphragm plane
LF—Light field diaphragm plane
S1—First point of intersection
S2—Second point of intersection
1—Microscope
2—Bright field illumination beam
3—Dark field illumination beam
4—Illumination beam path
5—Observation beam
6—Observation beam path
7—Light source
8—Collector
9—Illuminating lens
10—Condenser lens
11—Identification device
12—Splitter mirror
13—Dark field—objective
14—Objective lens system
15—Annular mirror
16—Object
17—Tube lens
18—Detector device
19—Color camera
20—Fully reflective ring
21—Partially transmissive circle
22—Bright field—objective
23—First external light source
24—Second external light source
25—Computer device
26—Light source for 2
27—Light source for 3
28—Diaphragm for 27
29—Diaphragm for 28
30—Additional splitter mirror
31—Further splitter mirror
32—First black & white camera
33—Second black & white camera
34—Color filter
35—Blue circle of 34 for 2
36—Red ring of 34 for 3
37—Opaque center stop for 28
38—Filter device
39—Illuminating device 40—Center ray of the bright field illuminating beam
41—Center ray of the dark field illuminating beam
42—Center axis of the observation beam path
43—Combined aperture diaphragm
44—Passage for bright field illumination
45—Passage for dark field illumination
46—Pin
47—Dark field annular lens

What is claimed is:

1. An apparatus for microscopic optical examination of a structured surface of an object, said apparatus comprising:

means for simultaneously illuminating the surface of the object in bright field and dark field with a plurality of illuminating beams in order to generate different images of the object;

an optical device associated with one of the illuminating beams for distinguishing the beam according to at least one property selected from the group consisting of color and polarization;

a filter for separating the light from the object according to the different illuminating beams, and a detector for detecting the different lights of the object or for separately evaluating different images of the object;

wherein a common incident light source is provided for bright field and dark field illumination and the device for distinguishing the illuminating beams is arranged in an aperture diaphragm plane of the illuminating beam path, and wherein the means for simultaneously illuminating the surface of the object includes an objective lens serving for the bright field illumination of the object and a coaxially arranged light reflecting means serving for the dark field illumination of the object, the objective lens collecting both of the different lights of the object or the different images of the object.

2. An apparatus according to claim 1, wherein said object is a semiconductor wafer or a mask for producing a structure on a semiconductor wafer.

3. An apparatus according to claim 1, further comprising a modulator for frequency or amplitude associated with the optical device for distinguishing the beam, and a matching demodulator associated with the filter for separating the light from the object.

* * * * *